(12) United States Patent
Pinchen et al.

(10) Patent No.: US 9,536,368 B2
(45) Date of Patent: Jan. 3, 2017

(54) AUTHENTICATION DEVICE

(71) Applicants: Stephen P. Pinchen, Derbyshire (GB); David Halliday, Nottinghamshire (GB)

(72) Inventors: Stephen P. Pinchen, Derbyshire (GB); David Halliday, Nottinghamshire (GB)

(73) Assignee: ESSENTRA PACKAGING & SECURITY LIMITED, Nottinghamshire (GB)

( * ) Notice: Subject to any disclaimer, the term of this patent is extended or adjusted under 35 U.S.C. 154(b) by 0 days.

(21) Appl. No.: 14/440,717

(22) PCT Filed: Nov. 6, 2013

(86) PCT No.: PCT/GB2013/052908
§ 371 (c)(1),
(2) Date: May 5, 2015

(87) PCT Pub. No.: WO2014/072707
PCT Pub. Date: May 15, 2014

(65) Prior Publication Data
US 2015/0287261 A1 Oct. 8, 2015

(30) Foreign Application Priority Data
Nov. 6, 2012 (GB) .................................. 1219915.4

(51) Int. Cl.
*G07D 7/12* (2016.01)
*G01N 21/64* (2006.01)

(52) U.S. Cl.
CPC ............ *G07D 7/121* (2013.01); *G01N 21/643* (2013.01); *G07D 7/128* (2013.01);
(Continued)

(58) Field of Classification Search
CPC ...... G07D 7/121; G07D 7/128; G01N 21/643; G01N 2021/6439; G01N 2201/062; G01N 2201/08
See application file for complete search history.

(56) References Cited

U.S. PATENT DOCUMENTS

| 6,409,088 B1 * | 6/2002 | Klevtsov ............ G06K 7/10762 235/454 |
| 2004/0051300 A1 | 3/2004 | Matsui et al. |

(Continued)

FOREIGN PATENT DOCUMENTS

| EP | 0 125 060 A2 | 11/1984 |
| EP | 1 164 553 A2 | 12/2001 |

(Continued)

OTHER PUBLICATIONS

Search Report of the United Kingdom Patent Office issued in Application No. GB1219915.4 dated Feb. 26, 2013 (3 pages).
(Continued)

*Primary Examiner* — Christine Sung
(74) *Attorney, Agent, or Firm* — Flynn, Thiel, Boutell & Tanis, P.C.

(57) ABSTRACT

There is disclosed an authentication device (10) for authenticating a luminescent security mark, the device comprising: an illumination source (30) configured to irradiate the security mark with a pulse of excitation radiation so as to cause the security mark to emit luminescent radiation that decays with time; a radiation detector configured to detect the luminescent radiation emitted by the security mark; and an optical waveguide (22) positioned relative to the illumination source (30) and the radiation detector and configured so as to guide by internal reflection both excitation radiation emitted from the illumination source towards the security mark, and luminescent radiation emitted by the security mark towards the radiation detector.

17 Claims, 3 Drawing Sheets

(52) U.S. Cl.
CPC .............. *G01N 2021/6439* (2013.01); *G01N 2201/062* (2013.01); *G01N 2201/08* (2013.01)

(56) References Cited

U.S. PATENT DOCUMENTS

| | | | |
|---|---|---|---|
| 2006/0202132 A1* | 9/2006 | Chua .................... | G01J 1/02 250/458.1 |
| 2006/0204145 A1* | 9/2006 | Vasic ................. | G06K 7/10831 382/321 |
| 2007/0165208 A1* | 7/2007 | Cowburn ............. | G03G 21/046 356/71 |
| 2007/0205377 A1 | 9/2007 | MacLeod et al. | |
| 2008/0048106 A1 | 2/2008 | Blanchard et al. | |
| 2009/0022390 A1 | 1/2009 | Yacoubian et al. | |
| 2010/0007930 A1* | 1/2010 | Cowburn ............. | G07D 7/2033 358/488 |

FOREIGN PATENT DOCUMENTS

| | | |
|---|---|---|
| EP | 2 290 622 A2 | 3/2011 |
| WO | WO 03/105075 A1 | 12/2003 |

OTHER PUBLICATIONS

International Search Report issued in PCT/GB2013/052908 with a mailing date of Feb. 13, 2014 (4 pages).

\* cited by examiner

AUTHENTICATION DEVICE

The invention relates to an authentication device for authenticating a security mark.

In the field of product or document security it is known to place a security mark on an article or its packaging, which can be read by a detector to identify the article and/or to verify the authenticity or otherwise of the article. Such a mark may typically be printed on the article, and may be invisible to the naked eye.

For example, there exist particularly sophisticated, complex inks which reliably emit radiation with certain characteristics under exposure to radiation in a certain frequency range. Such complex inks, which are by their nature difficult for counterfeiters to manufacture include inks known as taggant inks.

A taggant-ink marking on an article will, when exposed to appropriate radiation, exhibit behaviour of a certain signature or characteristic particular to that ink. For example, when the ink sample is irradiated by excitation radiation, the ink sample will emit luminescent radiation, and will continue to do so after exposure to the excitation radiation has ceased. The luminescent radiation decays in a known repeatable manner which is unique to the particular taggant.

One example of taggant material, as used in such complex inks, comprises a base material of lattice structure which includes one or more rare-earth metal dopants. By varying the level of dopant, or the position of dopant molecules within the lattice it is possible to produce a range of taggant materials which exhibit different, but predictable repeatable decay characteristics when excited by a pulse of radiation.

Typically an authentication device is used to provide the excitation radiation and then to detect emitted radiation so as to determine whether the mark is authentic. A typical detector measures the decay response of the mark and characterises the decay to determine if the mark is authentic. Previously considered authentication devices use a plurality of light emitting diodes (LEDs) as the illumination source. The LEDs are arranged at different angles such that they are directed towards a common illumination area located a distance away from the light emitting diodes. The focussing of the LEDs towards the common illumination area provides a "hotspot" of more intense light. It is therefore desirable to place the security mark at the position of this hotspot so as to maximise the radiation emitted from the luminescent material, thereby improving the accuracy of the authentication procedure. However, it may be difficult to reliably locate the security mark at the hotspot, particularly if the security mark is applied to a curved surface, for example. Moreover, the LEDs must be held in a plastic mount which defines the angular orientation of the light emitting diodes. However, the mount increases the size of the authentication device.

It is therefore desirable to provide an authentication device which performs an authentication procedure in an accurate and repeatable manner, whilst maintaining a compact design.

The invention is defined in the attached independent claim to which reference should now be made. Further, optional features may be found in the sub-claims appended thereto.

According to an aspect of the invention there is provided an authentication device for authenticating a luminescent security mark, the device comprising: an illumination source configured to irradiate the security mark with a pulse of excitation radiation so as to cause the security mark to emit luminescent radiation that decays with time; a radiation detector configured to detect the luminescent radiation emitted by the security mark; and an optical waveguide coupled to the illumination source and the radiation detector, the optical waveguide positioned relative to the illumination source and the radiation detector and configured so as to guide by internal reflection both excitation radiation emitted from the illumination source towards the security mark, and luminescent radiation emitted by the security mark towards the radiation detector.

The optical waveguide may have an internal surface which is adjacent the illumination source and the radiation detector and thus may be considered to be a proximal surface and an external surface which is spaced from the illumination source and the radiation detector and thus may be considered to be a distal surface. The optical waveguide may be configured to transmit light from one of the internal and external surfaces to the other of the internal and external surfaces.

The optical waveguide may be formed of a solid optical material, such as acrylic glass, which may be ultra clear Perspex. The sides of the optical material may be highly polished.

A side surface of the optical material may be covered by a cladding material which has a lower refractive index than that of the optical material. Accordingly, the cladding material may cause light to reflect at the interface between the optical material and the cladding material, thus preventing light from exiting the side surface of the optical material.

The optical waveguide may be substantially cuboidal. The optical waveguide may be elongate. The optical waveguide may have any suitable cross-sectional shape such as circular, oval, rectangular.

The illumination source and/or radiation detector may abut an internal surface of the optical waveguide.

The illumination source may comprise a substantially planar emitting surface which abuts a substantially planar internal surface of the optical waveguide.

The radiation detector may comprise a substantially planar receiving surface which abuts a substantially planar internal surface of the optical waveguide.

The authentication device may further comprise an optical glue disposed between the illumination source and/or radiation detector and an internal surface of the optical waveguide.

The illumination source comprises one or more light emitting diodes (LED).

The or each LED may be a surface mount LED. The or each surface mount LED may be mounted to a planar circuit board. The surface mount LEDs may allow the optical waveguide to be located closer to a PCB, thus reducing the axial length of the authentication device.

The illumination source may comprise a plurality of LEDs.

The plurality of LEDs may be oriented parallel to one another such that they emit excitation radiation in a common direction. In other words, the LEDs are not focussed towards a common illumination area. This may result in a more uniform distribution of light being emitted from the optical waveguide. Accordingly, the accuracy of the authentication process is less susceptible to the position of the security mark relative to the authentication device.

The plurality of LEDs may be disposed side-by-side along a linear line. The term "side-by-side" here does not require that the sides of the LEDs touch one another. The LEDs may be spaced apart from one another.

The authentication device may further comprise a visual security mark alignment guide on the outside of the authentication device and positioned on the linear line. The alignment guide indicate the position of the illumination source so as to aid alignment of the security mark with the illumination source. The alignment guide may be provided on a casing of the authentication device which surrounds the optical waveguide.

The radiation detector may comprise one or more photo-detectors. The or each photo-detector may be a surface mount photo-detector.

The invention may comprise any combination of the features and/or limitations referred to herein, except combinations of such features as are mutually exclusive.

For a better understanding of the present disclosure, and to show how it may be carried into effect, reference will now be made, by way of example, to the accompanying drawings, in which.

Figure 1:
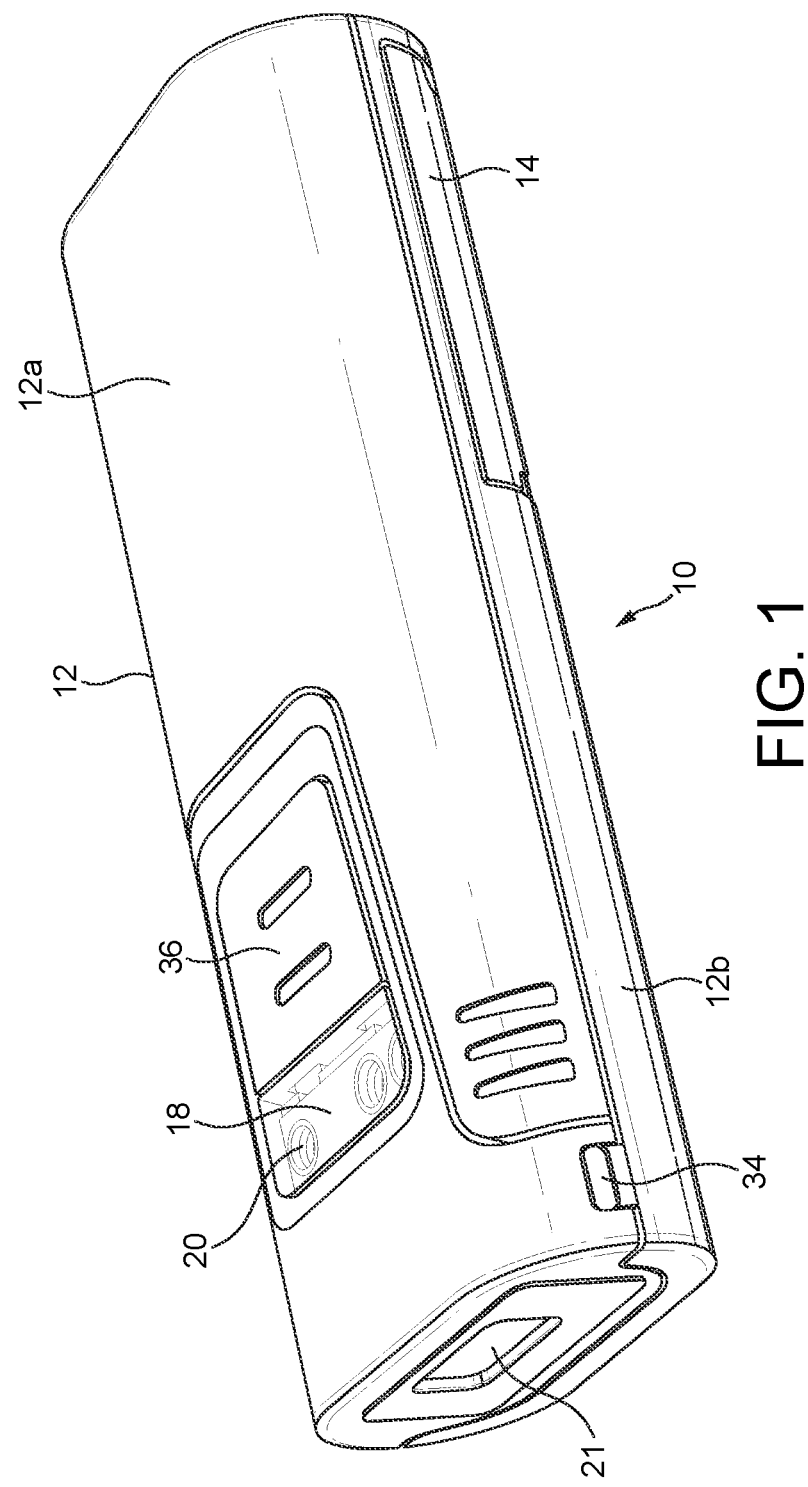
FIG. 1 is a perspective view of an authentication device according to an embodiment of the invention.

FIG. 1 shows an embodiment of an authentication device 10 for authenticating a luminescent security mark (otherwise known as a "taggant"). The authentication device 10 is a compact, pocket-sized device which may also be referred to as a fob reader. The authentication device 10 may be regarded as a portable, hand-held device due to its compact size and ergonomic shape, and by virtue of being battery-powered.

Figure 2:
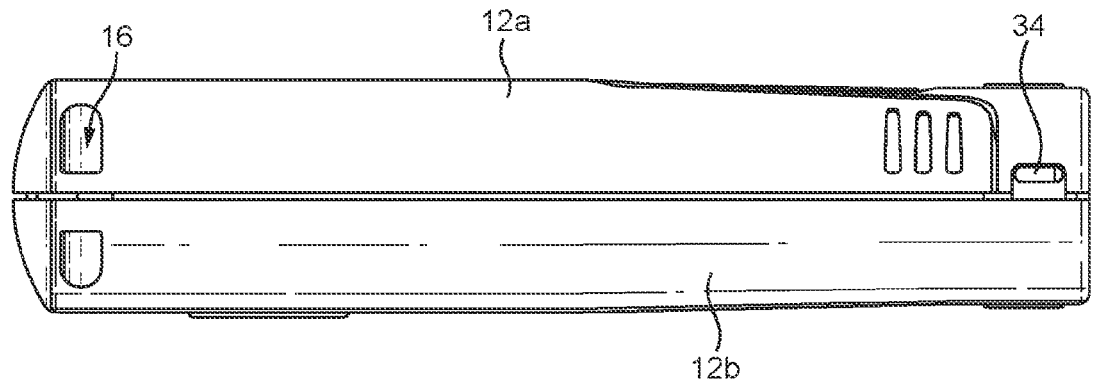
FIG. 2 is a side view of the authentication device of FIG. 1.
Figure 3:
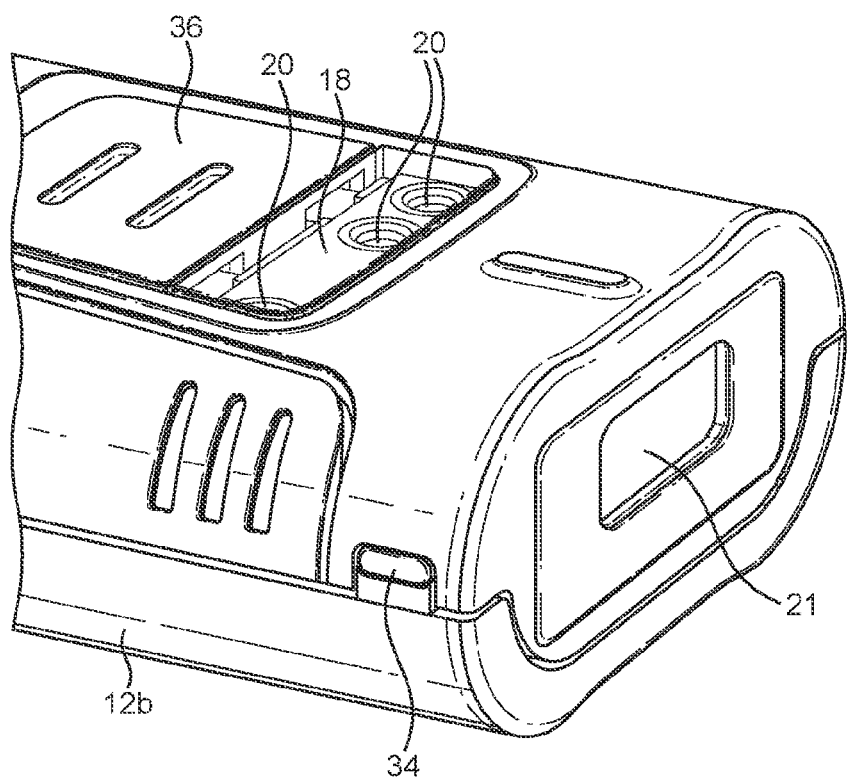
FIGS. 3 is an enlarged view of an end of the authentication device at which illumination/detection is performed.

With reference also to FIGS. 2 and 3, the authentication device 10 comprises an outer casing 12 which generally defines an elongate profile of substantially obround cross-section. The outer casing 12 is formed essentially of two sections, a front (or top) section 12a and a rear (or bottom) section 12b, which are connected to one another to encase the internal components of the authentication device 10, as will be described in more detail below.

The rear section 12b of the outer casing 12 comprises a battery compartment cover 14 which provides access to an internal battery compartment (not shown). The battery compartment cover 14 therefore allows a battery of the device to be accessed and replaced.

As shown in FIG. 2, the outer casing also defines an eye or through-hole 16. The eye 16 is defined by two cooperating through-holes formed at an upper end of the front and rear sections 12a, 12b of the outer casing 12. The eye 16 may be used to connect the authentication device 10 to a lanyard, such as a wrist or neck strap (not shown), using a cow hitch knot. The lanyard helps to prevent the authentication device 10 from being dropped and also allows the authentication device to be kept in an easily accessible and convenient location.

The outer casing 12 further comprises an indicator window 18 formed in the front section 12a of the outer casing 12. The indicator window 18 is transparent or translucent. The indicator window 18 is disposed over one or more indicator lights 20, such as light emitting diodes (LEDs), which allows the indicator lights 20 to be viewed by a user. As shown in FIG. 1, the authentication device 10 may comprise three indicator lights 20, the function of which will be described in more detail below. As shown particularly in FIG. 3, a cover member is disposed between the indicator lights 20 and the indicator window 18. The cover member is provided with complementary apertures which are aligned with the indicator lights 20. The cover member therefore enables the indicator lights 20 to be viewed through the indicator window 18 via the apertures of the cover member but obscures the underlying internal circuitry so that it cannot be seen through the indicator window 18. Alternatively, the indicator lights 20 may be mounted directly in the front section 12a of the outer casing 12 (using a similar arrangement to the cover member) without being covered by a window. The authentication device 10 is also provided with a sample button 36 which, as described in detail below, can be depressed to commence an authentication process.

An end surface of the outer casing 12 is provided with an aperture within which is disposed a lens 21 for filtering ambient light and against which an optical waveguide 22 abuts. This will be described in detail below.

The internal circuitry of the authentication device 10 will now be described with reference to FIG. 4. The internal circuitry comprises a main printed circuit board (PCB) 24, the dimensions of which correspond substantially to that of the outer casing 12. The main PCB 24 is provided with the necessary components for performing a processing procedure. The main PCB 24 also forms a connection with a power source which, as described previously and shown in FIG. 4, is preferably a battery 26.

An extension PCB 28 is connected to the main PCB 24. The extension PCB 28 is located towards a front end of the main PCB 24. The extension PCB 28 extends along the width of the main PCB 24 and is oriented orthogonally with respect to the main PCB 24. The extension PCB 28 and the main PCB 24 are both physically and electrically connected to one another. The dimensions of the extension PCB 28 correspond substantially to the cross-section of the outer casing 12 (taking into account the position of the main PCB 24).

The indicator lights 20 are provided on an upper surface of the extension PCB 28 with their emitting surfaces oriented so as to be parallel with the main PCB 24. The extension PCB 28 therefore holds the emitting surfaces of the indicator lights 20 against the cover member described previously so that they can viewed through the indicator window 18.

A lower surface of the extension PCB 28 is provided with an illumination source in the form of a two LEDs 30. The LEDs 30 may be infra-red LEDs that emit infra-red radiation having a wavelength of approximately 940 nm.

Figure 4:
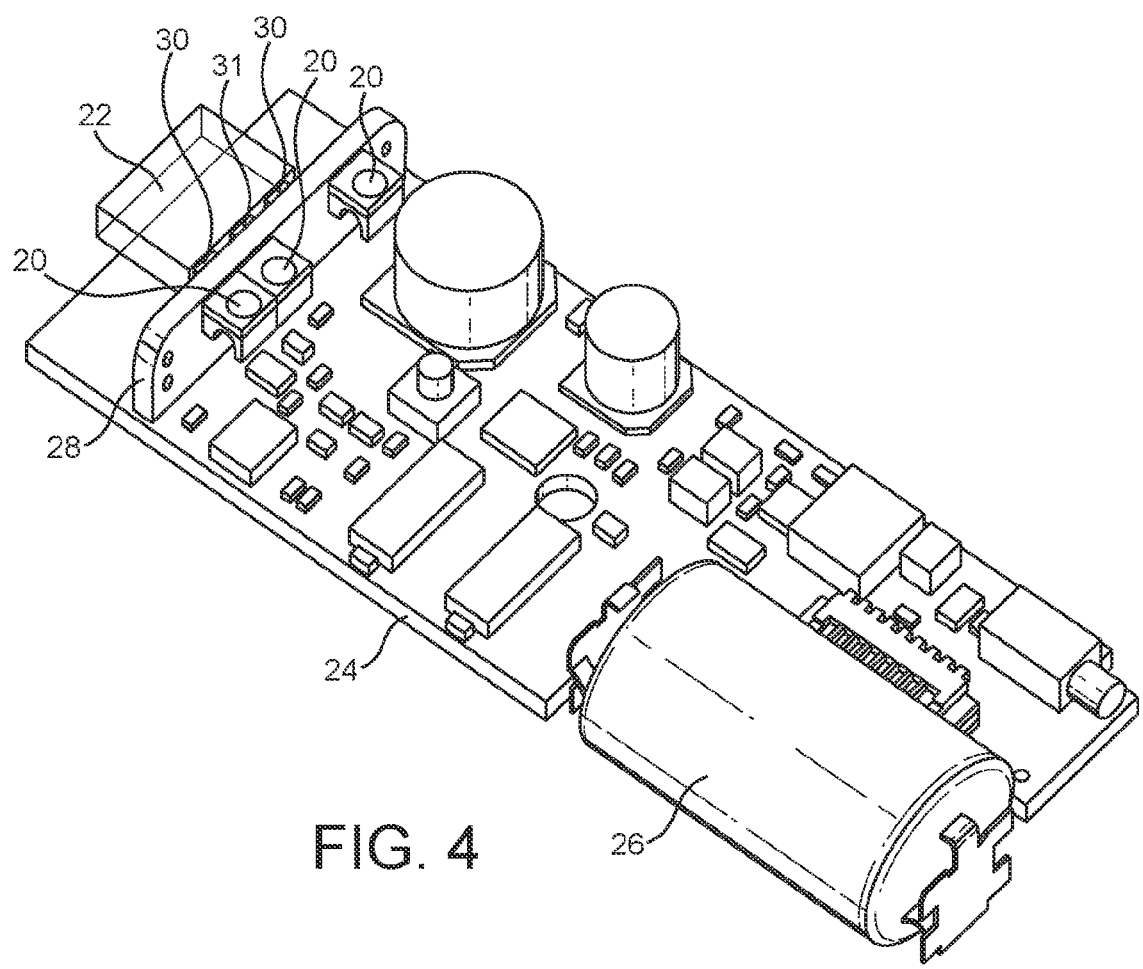
FIG. 4 schematically shows a perspective view of a printed circuit board found inside the authentication device.

The illumination source preferably comprises two LEDs 30 as shown in FIG. 4. In this embodiment the LEDs 30 are infrared LEDs that emit infrared light at a wavelength of around 940 nm. The LEDs 30 are surface mount components and thus have a low-profile. The LEDs 30 each have a substantially planar emitting surface which is coupled to an adjacent internal (with respect to the outer casing 12) surface of the optical waveguide 22. The internal surface of the optical waveguide 22 is also substantially planar such that the LEDs 30 abut intimately with the optical waveguide 22 across the emitting surfaces. The planar emitting surfaces of the LEDs 30 may be connected to the internal surface of the optical waveguide 22 using an optical glue to improve coupling.

The LEDs 30 are oriented on the extension PCB 28 such that they are parallel to one another. In other words, the planar emitting surfaces of the LEDs 30 are parallel with the extension PCB 28 and each lie in a common plane. Accordingly, the LEDs 30 are configured to emit excitation radiation in a common direction. Further, the LEDs 30 are arranged on the extension PCB 28 so that they are disposed side-by-side along a linear line.

The lower surface of the extension PCB 28 further comprises a radiation detector in the form of a photodetector 31 disposed between the two LEDs 30. The radiation detector 31 is arranged to detect infra-red radiation emitted from a security mark. Like the LEDs 30, the radiation detector 31 is also coupled to the internal surface of the optical waveguide 22. In this embodiment, the radiation detector 31 is a surface mount radiation detector having a substantially planar receiving surface which abuts the internal surface of the optical waveguide 22. As for the LEDs 30, the planar emitting surface of the radiation detector 31 may be connected to the internal surface of the optical waveguide 22 using an optical glue to improve coupling.

The optical waveguide 22 is essentially a cuboid formed of a solid optical material, such as acrylic glass (e.g. ultra clear Perspex) having all sides highly polished. However, the optical waveguide may alternatively have a circular or other suitable cross-section. The optical waveguide 22 is configured to transmit light from the internal surface to an external (with respect to the outer casing 12) surface, and vice versa. The optical waveguide 22 is positioned relative to the LEDs 30 and the radiation detector 31 and configured so as to guide both excitation radiation emitted from the LEDs towards a security mark, and luminescent radiation emitted by the security mark towards the radiation detector 31. For example, the optical waveguide 22 may transmit light between the internal and external surfaces via internal reflection.

If necessary, the side surfaces (i.e. the surfaces connecting the internal and external surfaces) of the optical waveguide 22 may be covered by a cladding material. The cladding material is selected so as to have a lower refractive index than that of the optical material. Consequently, light will be reflected at the interface between the optical material and the cladding material, thus preventing light from being lost from the side surfaces.

As described previously, an internal surface of the optical waveguide 22 is coupled to the illumination source (LEDs 30) and the radiation detector 31. The internal surface of the optical waveguide 22 is held in intimate contact with the LEDs 30 so as to minimise the light lost at the interface through reflection. The external surface of the optical waveguide 22 abuts the lens 21 which is received in an aperture provided at an end surface of the outer casing 12. Alternatively, the external surface of the optical waveguide 22 may be held against the end surface of the outer casing 12 such that the external surface is adjacent the aperture.

A visual security mark alignment guide 34 is provided on the outer casing 12 of the authentication device 10. There are two pairs of alignment guides 34, a first positioned on the linear line along which the LEDs 30 are disposed, and a second positioned perpendicular to the first. The alignment guide 34 provides a visual indication of the position of the LEDs 30 beneath the optical waveguide 22. Accordingly, the alignment guide 34 allows a user to easily align the security mark with the light emitted from the optical waveguide 22. The alignment guide 34 is preferably provided on the outer casing 12 so that it is visible when the end surface of the authentication device 10 is placed against a security mark. Alternatively or in addition, the alignment guide 34 may extend along the end surface of the authentication device 10.

The optical waveguide 22 is therefore able to transmit light (excitation radiation) generated by the illumination source from its internal surface to its external surface and out of the authentication device 10 through the lens 21. Similarly, the optical waveguide 22 is able to transmit light (luminescent radiation) generated externally to the authentication device 10 from its external surface to its internal surface and to the radiation detector 31.

The operation of the authentication device 10 and an automated authentication procedure will now be described in more detail.

In order to authenticate a luminescent security mark (or an article which may or should be provided with a security mark), the user places the end comprising the optical waveguide 22 of the authentication device 10 adjacent to a security mark to be verified. The security mark is aligned with the visual security mark alignment guide 34 which ensures that the optical waveguide 22 is over the security mark. The authentication device 10 may be able to authenticate a security mark which is located a short distance (i.e. in the region of 0-10 centimetres) away from the external surface of the optical waveguide 22.

Once aligned, the user triggers an authentication process by depressing the sample button 36. This starts a short warm-up sequence in which all of the electronic circuitry is activated. Following the warm-up sequence, the LEDs 30 are activated so as to generate a pulse of infra-red excitation radiation. The excitation radiation is transmitted by the optical waveguide 22 from its internal surface to its external surface where it is received by the security mark. The excitation radiation causes the security mark to emit luminescent radiation which decays with time. The emitted luminescent radiation is transmitted by the optical waveguide 22 from its external surface to its internal surface where it is received by the radiation detector 31.

The decay constant of the luminescent radiation is characteristic of the particular mark and can therefore be used to authenticate the mark. In this particular embodiment the decay response is characterised by measuring two intensity values at predetermined time intervals based on the radiation received at the radiation detector 31 and taking a ratio of the two intensity values. This ratio value can be compared with pre-stored reference values to determine if the mark is authentic.

In order to obtain accurate results, the mark is repeatedly illuminated and sampled a large number of times so as to obtain a set of ratio values. The set of ratio values is then averaged to give a sample. For example, 64 ratio values may be obtained and averaged. This process may be repeated a number of times (preferably in the order of 7 or 8). Each of the samples (i.e. the average values) is then allocated into one of a plurality of buckets. Each of the buckets covers a predefined but configurable range of values. The ranges of adjacent buckets need not be continuous. The ranges defined by each bucket may relate to a specific security mark or taggant material.

If a predefined number of samples fall within a single bucket, then the mark is deemed authentic. It may be necessary for the samples falling within that bucket to have been taken consecutively in order to gain a positive verification. On the other hand, if there are not sufficient samples in a single bucket, then the mark is not deemed to be authentic.

A positive and/or negative authentication may be signalled by the indicator lights 20. For example, a positive authentication may be signalled by a green LED, whereas a negative authentication may be signalled by a red LED. The authentication device 10 may also comprise an audible indication or vibration that the security mark has (or has not) been successfully authenticated.

As described previously, the LEDs 30 are arranged parallel to one another such that they emit excitation radiation in a common direction. The optical waveguide 22 acts to further collimate the excitation radiation through internal reflection within the optical waveguide 22. Consequently, the light emitted from the external surface of the optical waveguide 22 is substantially uniform. Accordingly, it is not necessary to position the security mark at a hot spot of the light in order to improve the accuracy of the authentication process. The authentication device of the present invention thus provides a more repeatable measurement which is less sensitive to measurement conditions. This allows measurements to be taken more quickly without sacrificing accuracy. Further, the optical waveguide 22 allows surface mount LEDs to be used as the illumination source. This considerably reduces the size of the authentication device 10.

Although the authentication device 10 has been described as being battery powered, it may also include an external power connector which allows the authentication device 10 to be connected to a mains power supply. This may be particularly beneficial where the authentication device 10 is being used for a prolonged period in a location where a mains power source is available. The external power connector could also be used to recharge the battery of the authentication device, if appropriate.

The authentication device may contain more than one radiation detector 31, where appropriate.

The authentication device 10 can be used in any orientation and thus the relative terms, such as upper and lower, used herein should not be considered prescriptive of a particular operative orientation.

The invention claimed is:

1. An authentication device for authenticating a luminescent security mark, the device comprising:
    an illumination source configured to irradiate the security mark with a pulse of excitation radiation so as to cause the security mark to emit luminescent radiation that decays with time;
    a radiation detector configured to detect the luminescent radiation emitted by the security mark; and
    an optical waveguide positioned relative to the illumination source and the radiation detector and configured so as to guide by internal reflection both excitation radiation emitted from the illumination source towards the security mark, and luminescent radiation emitted by the security mark towards the radiation detector, wherein the optical waveguide is formed of a solid optical material, and wherein a side surface of the optical material is covered by a cladding material, the cladding material having a lower refractive index than that of the optical material.

2. An authentication device as claimed in claim 1, wherein the optical material is acrylic glass.

3. An authentication device as claimed in claim 1, wherein the optical waveguide is substantially cuboidal.

4. An authentication device as claimed in claim 3, wherein the waveguide is elongate.

5. An authentication device as claimed in claim 1, wherein the illumination source and/or the radiation detector abuts an internal surface of the optical waveguide.

6. An authentication device as claimed in claim 5, wherein the illumination source comprises a substantially planar emitting surface which abuts a substantially planar internal surface of the optical waveguide.

7. An authentication device as claimed in claim 5, wherein the radiation detector comprises a substantially planar receiving surface which abuts a substantially planar internal surface of the optical waveguide.

8. An authentication device as claimed in claim 1, further comprising an optical glue disposed between the illumination source and/or the radiation detector and an internal surface of the optical waveguide.

9. An authentication device as claimed in claim 1, wherein the illumination source comprises at least one light emitting diode (LED).

10. An authentication device as claimed in claim 9, wherein the at least one LED is a surface mount LED.

11. An authentication device as claimed in claim 10, wherein the at least one surface mount LED is mounted to a planar circuit board.

12. An authentication device as claimed in claim 9, wherein the illumination source comprises a plurality of LEDs.

13. An authentication device as claimed in claim 12, wherein the plurality of LEDs are oriented parallel to one another such that they emit excitation radiation in a common direction.

14. An authentication device as claimed in claim 12, wherein the plurality of LEDs are disposed side-by-side along a linear line.

15. An authentication device as claimed in claim 14, further comprising a visual security mark alignment guide on the outside of the authentication device and positioned on the linear line.

16. An authentication device as claimed in claim 1, wherein the radiation detector comprises at least one photo-detector.

17. An authentication device as claimed in claim 16, wherein the at least one photo-detector is a surface mount photo-detector.

* * * * *